United States Patent [19]

Smith et al.

[11] Patent Number: 4,592,351
[45] Date of Patent: Jun. 3, 1986

[54] CANNULA HOLDER

[76] Inventors: Norma W. Smith, P.O. Box 319, Eagle Lake, Fla. 33830; Jonathan K. Bolin, 714 Flagway St., Kissimmee, Fla. 32758

[21] Appl. No.: 558,017

[22] Filed: Dec. 5, 1983

[51] Int. Cl.⁴ ............................................. A61M 16/00
[52] U.S. Cl. ............................ 128/207.17; 128/207.18
[58] Field of Search ....................... 248/454, 455, 127; 24/115 A, 129 B, 129 R; 174/170, 172; 128/207.14, 207.15, 207.17, 207.18

[56] References Cited

U.S. PATENT DOCUMENTS

| | | | |
|---|---|---|---|
| 1,350,860 | 8/1980 | Ersted | 24/129 B |
| 1,467,082 | 1/1922 | Baldwin | 248/127 |
| 3,046,989 | 7/1962 | Hill | 128/207.18 |
| 3,924,636 | 12/1975 | Addison | 128/351 |
| 3,946,742 | 3/1976 | Eross | 128/351 |
| 3,972,321 | 8/1976 | Proctor | 128/348 |
| 4,142,527 | 3/1979 | Garcia | 128/348 |
| 4,223,671 | 9/1980 | Muto | 128/200.26 |
| 4,249,529 | 2/1981 | Nestor et al. | 128/207.17 |
| 4,270,529 | 6/1981 | Muto | 128/200.26 |
| 4,316,459 | 2/1982 | Walski | 128/297.17 |
| 4,326,515 | 4/1982 | Shaffer et al. | 128/207.17 |
| 4,331,143 | 5/1982 | Foster | 128/207.17 |
| 4,331,144 | 5/1982 | Wapner | 128/207.17 |
| 4,333,468 | 6/1982 | Geist | 128/348 |
| 4,351,331 | 9/1982 | Gereg | 128/207.17 |
| 4,378,012 | 3/1983 | Brown | 128/207.17 |

Primary Examiner—Kyle L. Howell
Assistant Examiner—Daniel Haneiwich
Attorney, Agent, or Firm—Howson and Howson

[57] ABSTRACT

A holder for endotracheal or nasotracheal tubes comprises a plastic face guard, a plastic tube-grasping section with an adhesive foam pad, and a flexible section connecting the plastic face guard with the plastic tube-grasping section, the face guard, the tube-grasping section, and the flexible connecting section being a unitary sheet of plastic which, when flattened consists of two elongated parallel elements with a narrow flexible element connecting them and meeting each of them at an intermediate point of a long edge thereof.

4 Claims, 5 Drawing Figures

CANNULA HOLDER

BRIEF SUMMARY OF THE INVENTION

This invention relates to cannula holders, and more specifically to a device for holding endotracheal or nasotracheal tubes in place on a patient.

Endotracheal and nasotracheal tubes are cannulae used to maintain an open air passage for breathing under various circumstances. They are commonly used for the introduction of air and anesthetic during surgery, and are frequently used for considerable periods following surgery. They are also used in cases in which mechanical ventilation is required.

These tubes are typically held in place by means of adhesive tape, even though adhesive tape has numerous drawbacks. Adhesive tape often fails to hold the tube securely when it becomes wet. It has a tendency to bind and cause discomfort to the patient. It is difficult to apply, and once the tape is applied, it is difficult to adjust or reposition the tube. It is necessary to replace adhesive tape frequently. Adhesive tape has the further disadvantage that it does not readily permit cleaning of the mouth, including teeth and gums, or the application of suction to remove fluids from the mouth.

Although adhesive tape used for holding endotracheal and nasotracheal tubes in place has numerous disadvantages, it is still widely used. A number of special tube holders have been proposed, but they are generally either too complex, or unsatisfactory for other reasons.

The object of the present invention is to provide a holder which overcomes the various disadvantages of adhesive tape, and which is superior to other proposed cannula holders in the following respects individually and in combination. The cannula holder in accordance with the invention holds the cannula or tube securely in position while allowing for oral care. A single model accommodates various different sizes of tubes as well as various different kinds of tubes, including both endotracheal and nasotracheal tubes. The holder in accordance with the invention is extremely simple in structure and easy to use, comfortable to the patient, and neat in appearance. Unlike tape, it does not require frequent replacement. Furthermore, it may be affixed to the patient in different ways in order to accommodate different situations.

The cannula holder in accordance with the invention comprises a unitary sheet of flexible material such as polyvinyl chloride which, when flat, comprises first and second substantially parallel elongated strips connected together by a narrow section extending from an intermediate part of one long edge of the first strip to an intermediate part of one long edge of the second strip. A head band is provided which includes at least one stretchable elastic portion connected to both ends of the first strip. The second strip is provided with adhesive means on one of its faces, and is sufficiently flexible to be bent around the outside of a tube with the adhesive means in contact with the outside surface of the tube. The device may be attached to the tube simply by wrapping its adhesive-coated second strip around the tube. The narrow section of the sheet connecting the two elongated strips is sufficiently flexible to be bent so that, with the second strip bent around and attached to a tube entering the patient's mount in a direction substantially perpendicular to the region of the patient's face surrounding the mouth, a face of the first strip can rest comfortably against a part of said region, either between the patient's upper lip and nose, or between the patient's lower lip and chin.

The stretchable elastic portion of the head band permits temporary movement of the holder for oral care. Preferably, the head band includes two stretchable elastic portions connected to opposite ends of the first strip. Also, preferably the head band comes in two parts which are attachable to each other for easy and rapid application and removal of the holder.

The narrow section of the sheet is preferably sufficiently flexible to be bent back on itself at angle of approximately 180 degrees so that the holder can be used with a nasotracheal tube.

Further objects and advantages of the invention will be apparent from the following detailed description when read in conjunction with the drawings.

DETAILED DESCRIPTION

Figure 1:
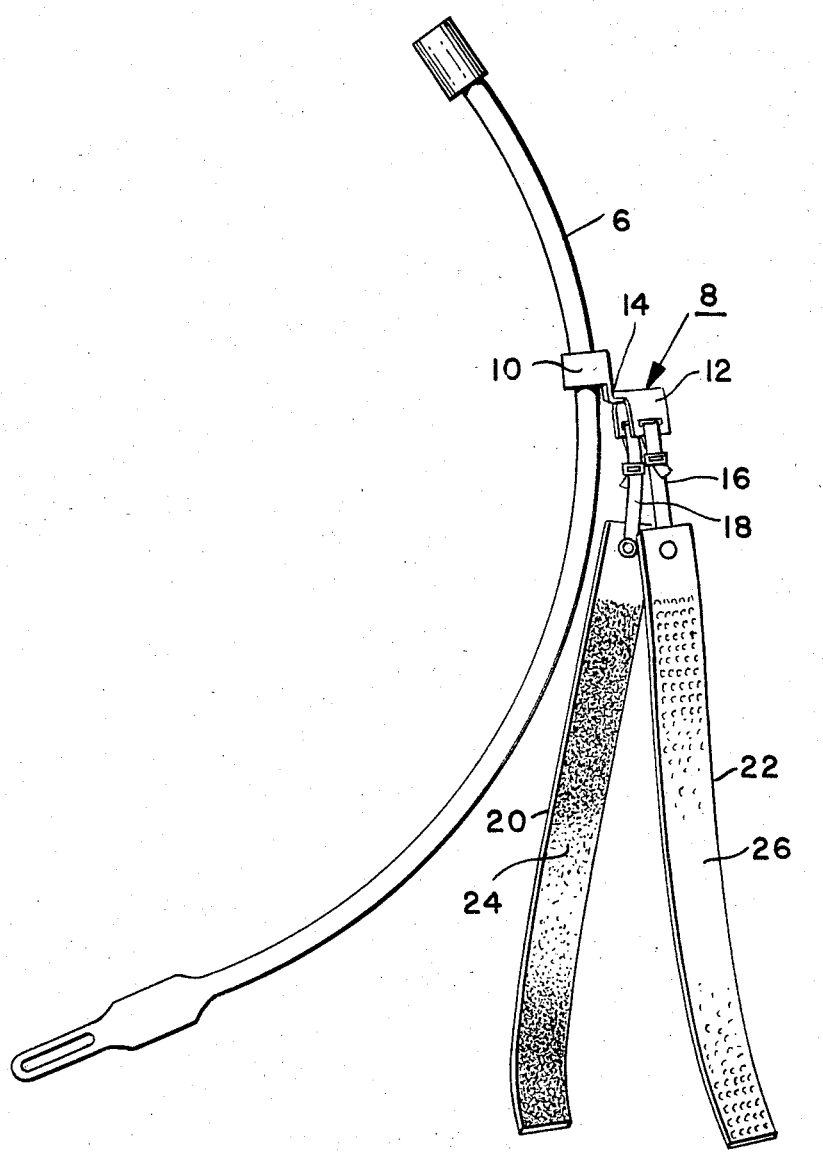
FIG. 1 is a side elevation of a typical endotracheal tube showing a holder in accordance with the invention attached to it.

FIG. 1 shows the curved tubular body 6 of an endotracheal tube with the holder in accordance with the invention attached to it. (This is an artificial depiction of the invention, as normally the endotracheal tube will be inserted into the patient's mouth before the holder is attached.) The holder comprises a flexible sheet 8 having a tube-grasping part 10, and a face guard 12, connected together by a narrow flexible section 14. Elastic strips 16 and 18 are secured to opposite ends of face guard 12, and head band sections 20 and 22 are connected respectively to the ends of elastic strips 18 and 16 remote from the face guard. The head band sections 20 and 22 are faced with the complementary parts of a Velcro fastener, the fuzz or looped part 24 being located on the inside face of head band section 20, and the hook part 26 being located on the outside face of band section 22.

Figure 2:
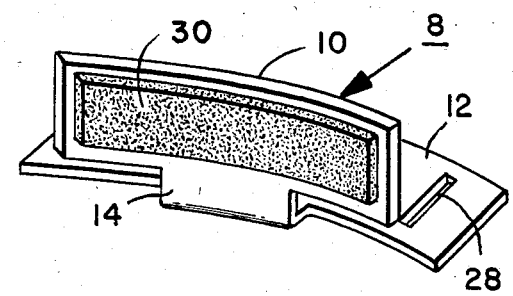
FIG. 2 is a perspective view of the flexible sheet portion of the holder comprising two elongated strips connected together by a flexible section, one of the strips having adhesive means thereon.

The flexible sheet 8 is shown in more detail in FIG. 2. It comprises a single sheet of flexible material such as polyvinyl chloride (PVC) or similar material which, when flat, is in a generally I-shaped configuration with the tube-grasping part 10 and the face guard 12 in the form of generally parallel, elongated sections. These two sections are connected together by a narrow flexible section 14. Section 14 is bent at an angle of 90 degrees when the holder is used with an endotracheal tube. However, it should be capable of being bent a full 180 degrees for use with a nasotracheal tube.

Face guard 12 is designed to rest against a region of the patient's face adjacent to the mouth, and is provided with a pair of slots, one of which is shown at 28, for attachment of elastic strips 16 and 18 (FIG. 1).

Narrow flexible section 14 extends from one long edge of face guard 12 to one long edge of tube-grasping part 10. Section 14 should be sufficiently narrow as to allow section 10 to be bent around an endotracheal or nasotracheal tube. The width of section 14 is typically about 1.5 cm. One face of tube-grasping part 10 is provided with a foam pad 30 having an adhesive coating on both of its sides. The adhesive coating on one side secures the pad to part 10, and the adhesive coating on the other side is available for secure attachment of the device to an endotracheal or nasotracheal tube. The length of tube-grasping part 10 and its adhesive-coated foam pad can be cut down easily to accommodate smaller diameter tubes.

Figure 3:
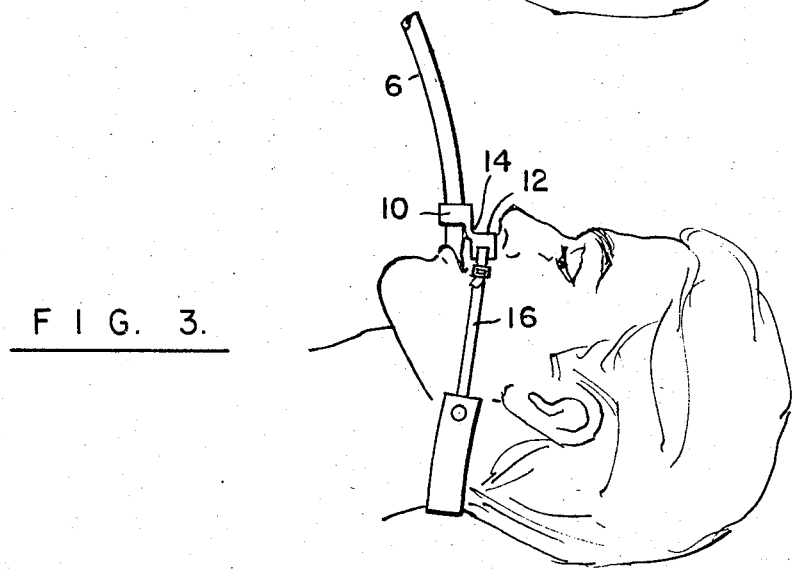
FIG. 3 is a side elevation of the head of a patient showing an endotracheal tube held in place by a holder in accordance with the invention, where the holder rests against the region of the patient's face between the nose and the upper lip.

FIG. 3 shows the holder connected to an endotracheal tube 6, with face guard 12 against the region of the patient's face between the upper lip and the nose. The elastic strips permit the endotracheal tube to be moved without detachment of the tube holder. Thus, the patient's mouth can be cleaned, or suction applied to remove secretions without the need for detachment and reattachment of the tube holder.

Figure 4:
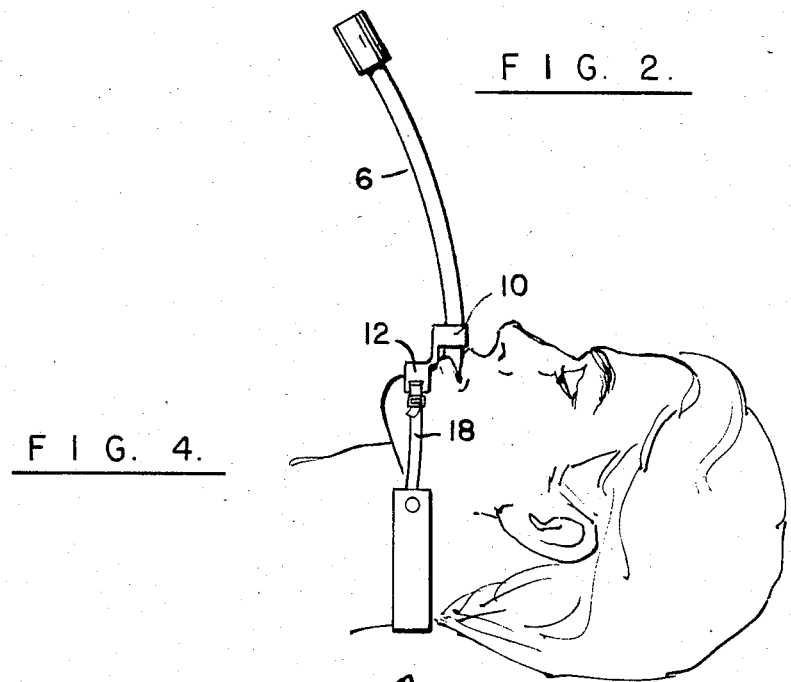
FIG. 4 is an elevation of a patient with an endotracheal tube held in place by a holder in accordance with the invention, where the holder rests against the region of the patient's face between the lower lip and the chin.

The holder may also be positioned as shown in FIG. 4, with the face guard 12 against the region of the patient's face between the lower lip and the chin. Here again, the elastic strips permit the endotracheal tube and the tube-grasping part to be moved for cleaning of the patient's mouth without the need for detachment and reattachment.

Figure 5:
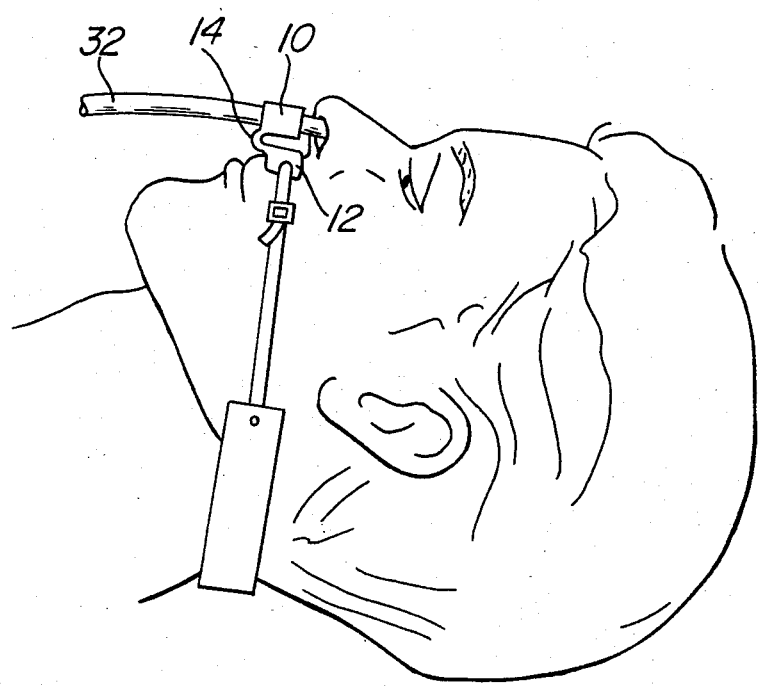
FIG. 5 is an elevation of a patient with a nasotracheal tube held in place by a holder in accordance with the invention.

In the case of a nasotracheal tube, the face guard 12 is positioned as shown in FIG. 5, and the narrow flexible section 14 is bent at an angle of approximately 180 degrees so that the tube-grasping part is directly above the face guard. In this position, tube-grasping part 10 can be wrapped around and secured to a nasotracheal tube 32 to hold it securely.

The cannula holder of the invention, by virtue of the Velcro head band sections can be used with virtually any patient, regardless of age or size. Furthermore, the head band sections provide for adjustment of the elastic strips to any desired level of tension, since Velcro fasteners are adjustable to any position, not merely to discrete positions. The cannula holder of the invention can be made very inexpensively, and therefore, even though it can be used with a given patient over a lengthy course of treatment without replacement, it can be disposed of after the patient no longer has need for it.

We claim:

1. A cannula holder comprising:
   a unitary sheet of flexible material having front and rear faces and capable of being flattened so that its faces lie in planes and which, when so flattened, comprises first and second substantially parallel elongated rectangular strips connected together by a narrow section extending from an intermediate part of one long edge of the first strip to an intermediate part of one long edge of the second strip;
   a head band including at least one stretchable elastic portion, connected to both ends of said first strip; and
   adhesive means on one face of the second strip;
   the second strip being sufficiently flexible to be bent around the outside of a tube with said adhesive means in contact with the outside surface of the tube, the narrow section of the sheet being sufficiently flexible to be bent both at an angle of approximately 90 degrees, and back on itself at an angle of approximately 180 degrees, so that, with a face of the first strip resting confortably against a part of the region of a patient's face surrounding the mouth, the second strip can be bent around an endotracheal tube entering the patient's mouth or alternatively around a nasotracheal tube entering the patient's nose.

2. A holder according to claim 1 in which the head band includes a first stretchable elastic portion connected directly at one of its ends to one end of the first strip, a second stretchable elastic portion connected directly at one of its ends to the other end of the first strip, a first flexible band attached to the end of one of said elastic portions remote from the first strip, and a second flexible band attached to the end of the other of said elastic portions remote from the first strip, said first and second flexible bands having interengageable means for attachment of said bands together to form a loop around the patient's head.

3. A holder according to claim 2 in which the interengageable means are engageable with each other through a substantially continuous range of relative positions for adjustment of the length of the head band to any desired length within a range of lengths.

4. A holder according to claim 1 in which the adhesive means is a flexible pad of foam material coated on one side with an adhesive material adhering it to said one face of the second strip and on its other side with an adhesive material capable of adhering to a tube.

* * * * *